(12) United States Patent
Becker et al.

(10) Patent No.: US 6,423,517 B2
(45) Date of Patent: *Jul. 23, 2002

(54) GRANULE CONTAINING PROTEIN AND SALT LAYERED ON AN INERT PARTICLE

(75) Inventors: Nathaniel T. Becker, Burlingame; Robert I. Christensen, Jr., Pinole, both of CA (US); Ernst H. Gros, Kantvik (FI)

(73) Assignee: Genecor International, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/215,086

(22) Filed: Dec. 18, 1998

Related U.S. Application Data

(63) Continuation-in-part of application No. 08/995,430, filed on Dec. 20, 1997, now abandoned.

(51) Int. Cl.$^7$ .............................. C12N 9/98; C12N 9/96; C12N 11/00; C07K 17/00; A61K 9/16
(52) U.S. Cl. ..................... 435/187; 424/489; 435/188; 435/174; 435/176; 435/178; 435/180; 530/810; 530/811; 530/813; 530/815
(58) Field of Search ................................ 435/187, 188, 435/174, 176, 177, 178, 179, 180; 530/402, 810, 811, 812, 813, 814, 815; 424/489

(56) References Cited

U.S. PATENT DOCUMENTS

| | | | | |
|---|---|---|---|---|
| 4,106,991 A | | 8/1978 | Markussen et al. | 435/187 |
| 4,689,297 A | * | 8/1987 | Good et al. | 435/174 |
| 4,740,469 A | | 4/1988 | Nishinaka et al. | 435/187 |
| 4,760,025 A | | 7/1988 | Estell et al. | 435/222 |
| 5,324,649 A | | 6/1994 | Arnold et al. | 435/187 |
| 5,814,501 A | * | 9/1998 | Becker et sl. | 435/174 |
| 5,879,920 A | * | 3/1999 | Dale et al. | 435/187 |

FOREIGN PATENT DOCUMENTS

| | | |
|---|---|---|
| EP | 0 304 332 A2 | 2/1989 |
| EP | 0 130 756 B1 | 6/1991 |
| EP | 0 532 777 A1 | 3/1993 |
| WO | WO 91/06637 | 5/1991 |
| WO | WO 91/09941 | 7/1991 |
| WO | WO 97/12958 | 4/1997 |
| WO | WO 97/23606 | 7/1997 |
| WO | WO 98/55577 | 12/1998 |
| WO | WO 99/32595 | 7/1999 |
| WO | WO 99/32612 | 7/1999 |
| WO | WO 99/32613 | 7/1999 |

OTHER PUBLICATIONS

Gaertner, A.L., et al., "Development of low dust enzyme detergent granules with high storage stability," Proc. Int. Symp. Controlled Release Bioact. Mater. (1998) 25$^{th}$, 289–290 Coden: PCRMEY; ISSN: 1022–0178 (XP002102189).

* cited by examiner

*Primary Examiner*—David M. Naff
(74) *Attorney, Agent, or Firm*—Genecor International, Inc.

(57) ABSTRACT

Granules are prepared containing an admixture of protein and salt layered over an inert particle. A preferred amount of salt is about between 63.7 and 84.3% of the total weight of the admixture. Proteins include pharmaceutically important proteins such as hormones, or industrially important proteins such as enzymes including proteases, amylases, lipases and cellulases capable of hydrolyzing substrates such as stains. Inert particles include inorganic salts, sugars, sugar alcohols, small organic molecules such as organic acids or salts, and minerals such as clays or silicates. A binder such as starch or polyethylene oxide may be mixed in with the admixture. A barrier material such as an inorganic salt or organic acid or salt may be in the admixture or coated over the admixture layer. A coating layer of a soluble or water dispersible film-forming polymer may be between the inert particle and admixture layer and/or over the admixture layer. The granules may also contain plasticizers, extenders, lubricants, pigments and anti-agglomeration agents. A preferred method for preparing the granules is by spraying a solution or slurry of the admixture onto the inert particles while fluidized in a fluid-bed coater.

26 Claims, No Drawings

GRANULE CONTAINING PROTEIN AND SALT LAYERED ON AN INERT PARTICLE

RELATED APPLICATIONS

This application is a continuation-in-part of U.S. patent application Ser. No. 08/995,430 filed Dec. 20, 1997, now abandoned, all of which is hereby incorporated herein in its entirety.

BACKGROUND OF THE INVENTION

Proteins such as pharmaceutically important proteins like hormones and industrially important proteins like enzymes are becoming more widely used. Enzymes, for example, are used in several industries including, for example, the starch industry, the dairy industry, and the detergent industry. It is well known in the detergent industry that the use of enzymes, particularly proteolytic enzymes, has created industrial hygiene concerns for detergent factory workers, particularly due to the health risks associated with dustiness of the available enzymes.

Since the introduction of enzymes into the detergent business, many developments in the granulation and coating of enzymes have been offered by the industry. See for example the following patents relating to enzyme granulation:

U.S. Pat. No. 4,106,991 describes an improved formulation of enzyme granules by including within the composition undergoing granulation, finely divided cellulose fibers in an amount of 2–40% w/w based on the dry weight of the whole composition. In addition, this patent describes that waxy substances can be used to coat the particles of the granulate.

U.S. Pat. No. 4,689,297 describes enzyme containing particles which comprise a particulate, water dispersible core which is 150–2,000 microns in its longest dimension, a uniform layer of enzyme around the core particle which amounts to 10%–35% by weight of the weight of the core particle, and a layer of macro-molecular, film-forming, water soluble or dispersible coating agent uniformly surrounding the enzyme layer wherein the combination of enzyme and coating agent is from 25–55% of the weight of the core particle. The core material described in this patent includes clay, a sugar crystal enclosed in layers of corn starch which is coated with a layer of dextrin, agglomerated potato starch, particulate salt, agglomerated trisodium citrate, pan crystallized NaCl flakes, bentonite granules or prills, granules containing bentonite, Kaolin and diatomaceous earth or sodium citrate crystals. The film forming material may be a fatty acid ester, an alkoxylated alcohol, a polyvinyl alcohol or an ethoxylated alkylphenol.

U.S. Pat. No. 4,740,469 describes an enzyme granular composition consisting essentially of from 1–35% by weight of an enzyme and from 0.5–30% by weight of a synthetic fibrous material having an average length of from 100–500 micron and a fineness in the range of from 0.05–0.7 denier, with the balance being an extender or filler. The granular composition may further comprise a molten waxy material, such as polyethylene glycol, and optionally a colorant such as titanium dioxide.

U.S. Pat. No. 5,254,283 describes a particulate material which has been coated with a continuous layer of a non-water soluble, warp size polymer. U.S. Pat. No. 5,324,649 describes enzyme-containing granules having a core, an enzyme layer and an outer coating layer. The enzyme layer and, optionally, the core and outer coating layer contain a vinyl polymer.

WO 91/09941 describes an enzyme containing preparation whereby at least 50% of the enzymatic activity is present in the preparation as enzyme crystals. The preparation can be either a slurry or a granulate.

WO 97/12958 discloses a microgranular enzyme composition. The granules are made by fluid-bed agglomeration which results in granules with numerous carrier or seed particles coated with enzyme and bound together by a binder.

It would be desirable to produce enzyme granules with improved stability, particularly in bleach-containing detergents at high humidity and temperature. Current fluid-bed spray-coated enzyme granules contain the enzyme in a relatively thin layer near the surface of the granule. This geometry renders the enzyme more vulnerable being chipped off of the granule in a concentrated layer during handling and conveying operations, increasing the likelihood and levels of airborne enzyme aerosols in the working environment. This geometry also makes the enzyme more vulnerable to attack by penetrating moisture and inactivating substances.

However, even in light of these developments offered by the industry (as described above) there is a continuing need for low-dust enzyme granules which have additional beneficial characteristics. Additional beneficial characteristics needed in the enzyme granulation industry are low-residue granule formulations (where low residue is defined as a reduced tendency to leave noticeable undissolved residues on clothes or other material), and improved stability formulations. Accomplishing all these desired characteristics simultaneously is a particularly challenging task since, for example, many delayed release or low-dust agents such as fibrous cellulose or warp size polymers leave behind insoluble residues.

As such, there is a need for, for example, a detergent enzyme granule which is simultaneously non-dusting, stable when stored in detergents, and easy to manufacture in a controlled size distribution. Granules of a controlled size distribution are desirable in order to impart good flowability properties for handling and blending into detergents, and to resist segregation and settling once formulated into detergents.

Therefore, it is an object of the present invention to provide low-dust, low residue, highly soluble enzyme granules having increased stability. It is another object of the present invention to provide processes which afford the formation of such improved granules.

SUMMARY OF THE INVENTION

The present invention provides a granule that includes a protein core that includes an protein matrix layered on a seed particle. The protein matrix includes a protein mixed together with a salt and optionally, a binder. Optionally, a coating can be applied, for example, to the seed particle or over the protein matrix.

The present invention further provides a granule that includes an enzyme core that includes an enzyme matrix layered on a seed particle. The enzyme matrix includes an enzyme mixed together with a salt and optionally, a binder. Optionally, a coating can be applied, for example, to the seed particle or over the enzyme matrix.

The present invention also provides a method for making granules including fluidizing seed particles in a fluidized bed coater; providing a protein matrix formula comprising protein mixed together with a salt; and spraying the protein matrix formula onto the seed particles. Optionally, a coating can be applied, for example, to the seed particle or over the enzyme matrix.

The present invention further provides a method for making granules including fluidizing seed particles in a fluid-bed coater; providing an enzyme matrix formula comprising enzyme mixed together with a salt; and spraying the enzyme matrix formula onto the seed particles. Optionally, a coating can be applied, for example, to the seed particle or over the enzyme matrix.

DETAILED DESCRIPTION OF THE INVENTION

One embodiment of the invention is a granule that includes a protein core that includes a protein matrix layered over a seed particle. The protein matrix includes a protein mixed together with a salt. Optionally, a coating can be applied, for example, to the seed particle or over the enzyme matrix.

Another embodiment of the invention is a granule that includes an enzyme core that includes an enzyme matrix layered over a seed particle. The enzyme matrix includes an enzyme mixed together with a salt. Optionally, a coating can be applied, for example, to the seed particle or over the enzyme matrix.

A further embodiment of the invention is a method for making granules including fluidizing seed particles in a fluid-bed coater; providing a protein matrix formula comprising protein mixed together with a salt; and spraying the protein matrix formula onto the seed particles. Optionally, a coating can be applied, for example, to the seed particle or over the enzyme matrix.

Yet another embodiment of the invention is a method for making granules including fluidizing seed particles in a fluid-bed coater; providing an enzyme matrix formula comprising enzyme mixed together with a salt; and spraying the enzyme matrix formula onto the seed particles. Optionally, a coating can be applied, for example, to the seed particle or over the enzyme matrix.

A "protein core", an "enzyme core" or a "core" includes a protein matrix, for example, an enzyme matrix in the case of an enzyme core. There can be one or more layers between the seed particle and the matrix, for example, a coating such as polyvinyl alcohol.

Seed particles are inert particles upon which the enzyme matrix can be layered which are composed of inorganic salts, sugars, sugar alcohols, small organic molecules such as organic acids or salts, minerals such as clays or silicates or a combination of two or more of these. Suitable soluble ingredients for incorporation into seed particles include: sodium chloride, potassium chloride, ammonium sulfate, sodium sulfate, sodium sesquicarbonate, urea, citric acid, citrate, sorbitol, mannitol, oleate, sucrose, lactose and the like. Soluble ingredients can be combined with dispersible ingredients such as talc, kaolin or bentonite. Seed particles can be fabricated by a variety of granulation techniques including: crystallization, precipitation, pan-coating, fluid-bed coating, fluid bed agglomeration, rotary atomization, extrusion, prilling, spheronization, drum granulation and high shear agglomeration. In the granules of the present invention, the ratio of seed particles to granules is 1:1.

The "protein matrix", "enzyme matrix" or "matrix" is an admixture of one or more proteins such as an enzyme and a salt. The protein and salt can be mixed, for example, in solution or as a slurry to form the "protein matrix formula", "enzyme matrix formula" or "matrix formula" that is applied to the seed particle. The salt content of the admixture preferably contains about between 63.7 to 85.3% salt based on dry solids as shown in Examples 1–4. The protein can be applied from a solution or applied in slurry form as a suspension of crystals or precipitated protein.

By burying a protein within a matrix, the protein can be better protected from the twin dangers of attrition and activity loss. Also, to achieve a low dusting granular protein product, it is necessary to control the shape and size distribution of the granules. Uniform and reproducible size and shape also contribute to granule stability, since particle breakup and re-agglomeration would bring some protein near the granule surface.

Salts that can be used in the present invention include those where the cation is sodium, potassium, magnesium, calcium, zinc or aluminum and where the anion is chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, stearate, laurate, palmitate, oleate, ascorbate or gluconate. Preferred salts include magnesium sulfate, sodium citrate, sodium chloride, sodium sulfate, potassium sulfate, ammonium sulfate, potassium chloride, magnesium acetate. One or more salts can be used in the matrix. The matrix of the present invention comprises between about 20–80% of the final granule weight.

The granules of the present invention can also be adjusted to a particular pH or pH range by adding the acid or base form of the salt or salts used.

Proteins that are within the scope of the present invention include pharmaceutically important proteins such as hormones or other therapeutic proteins and industrially important proteins such as enzymes.

Any enzyme or combination of enzymes may be used in the present invention. Preferred enzymes include those enzymes capable of hydrolyzing substrates, e.g. stains. These enzymes are known as hydrolases which include, but are not limited to, proteases (bacterial, fungal, acid, neutral or alkaline), amylases (alpha or beta), lipases, cellulases and mixtures thereof. Particularly preferred enzymes are subtilisins and cellulases, Most preferred are subtilisins such as described in U.S. Pat. No. 4,760,025, EP Patent 130 756 B1 and EP Patent Application WO 91/06637, which are incorporated herein by reference, and cellulases such as Multifect L250™ and Puradax™, commercially available from Genencor International. Other enzymes that can be used in the present invention include oxidases, transferases, dehydratases, reductases, hemicellulases and isomerases.

The matrix of the granules of the present invention may further comprise one or more binders or other excipients as known to those skilled in the art. Suitable binders include natural polymers such as starch, modified starch, carrageenan, gum arabic and guar gum and synthetic polymers such as polyethylene oxide, polyvinyl pyrrolidone, polyethylene glycol and polyethylene oxide/polypropylene oxide.

The matrix may also further comprise plasticizers for the binder and anti-agglomeration agents. Suitable plasticizers useful in the present invention include polyols such as glycerol, propylene glycol, polyethylene glycol (PEG), urea, or other known plasticizers such as triethyl citrate, dibutyl or dimethyl phthalate or water. Suitable anti-agglomeration agents include fine insoluble and sparingly soluble material such as talc, $TiO_2$, clays, amorphous silica, magnesium stearate, stearic acid and calcium carbonate.

The granules of the present invention can further comprise a barrier layer. A barrier layer is used to slow or prevent the diffusion of substances that can adversely affect the protein or enzyme into the matrix. The barrier layer is made up of a barrier material and can be coated over the protein core or the barrier material can be included in the protein core. Suitable barrier materials include, for example, inorganic salts or organic acids or salts.

The granules of the present invention can further also comprise one or more coating layers. For example, such coating layers may be one or more intermediate coating layers, or such coating layers may be one or more outside coating layers or a combination thereof. Coating layers may serve any of a number of functions in a granule composition, depending on the end use of the enzyme granule. For example, coatings may render the enzyme resistant to oxidation by bleach, bring about the desirable rates of dissolution upon introduction of the granule into an aqueous medium, or provide a barrier against ambient moisture in order to enhance the storage stability of the enzyme and reduce the possibility of microbial growth within the granule.

Suitable coatings include water soluble or water dispersible film-forming polymers such as polyvinyl alcohol (PVA), polyvinyl pyrrolidone (PVP), cellulose derivatives such as methylcellulose, hydroxypropyl methylcellulose, hydroxycellulose, ethylcellulose, carboxymethyl cellulose, hydroxypropyl cellulose, polyethylene glycol, polyethylene oxide, gum arabic, xanthan, carrageenan, chitosan, latex polymers, and enteric coatings. Furthermore, coating agents may be used in conjunction with other active agents of the same or different categories.

Suitable PVAs for incorporation in the coating layer(s) of the granule include partially hydrolyzed, fully hydrolyzed and intermediately hydrolyzed PVAs having low to high degrees of viscosity. Preferably, the outer coating layer comprises partially hydrolyzed PVA having low viscosity. Other vinyl polymers which may be useful include polyvinyl acetate and polyvinyl pyrrolidone. Useful copolymers include, for example, PVA-methylmethacrylate copolymer and PVP-PVA copolymer.

The coating layers of the present invention may further comprise one or more of the following: plasticizers, extenders, lubricants, pigments, and optionally additional enzymes. Suitable plasticizers useful in the coating layers of the present invention are plasticizers including, for example, polyols such as sugars, sugar alcohols, or polyethylene glycols (PEGs), urea, glycol, propylene glycol or other known plasticizers such as triethyl citrate, dibutyl or dimethyl phthalate or water. Suitable pigments useful in the coating layers of the present invention include, but are not limited to, finely divided whiteners such as titanium dioxide or calcium carbonate or colored pigments and dyes or a combination thereof. Preferably such pigments are low residue pigments upon dissolution. Suitable extenders include sugars such as sucrose or starch hydrolysates such as maltodextrin, corn syrup solids, clays such as kaolin and bentonite and talc. Suitable lubricants include nonionic surfactants such as Neodol, tallow alcohols, fatty acids, fatty acid salts such as magnesium stearate and fatty acid esters.

Adjunct ingredients may be added to the enzyme granules of the present invention. Adjunct ingredients may include: metallic salts; solubilizers; activators; antioxidants; dyes; inhibitors; binders; fragrances; enzyme protecting agents/scavengers such as ammonium sulfate, ammonium citrate, urea, guanidine hydrochloride, guanidine carbonate, guanidine sulfamate, thiourea dioxide, monoethanolamine, diethanolamine, triethanolamine, amino acids such as glycine, sodium glutamate and the like, proteins such as bovine serum albumin, casein and the like etc.; surfactants including anionic surfactants, ampholytic surfactants, nonionic surfactants, cationic surfactants and long-chain fatty acid salts; builders; alkalis or inorganic electrolytes; bleaching agents; bluing agents and fluorescent dyes and whiteners; and caking inhibitors.

The granules described herein may be made by methods known to those skilled in the art of enzyme granulation specifically fluid-bed coating.

The following examples are representative and not intended to be limiting. One skilled in the art could choose other proteins, enzymes, matrices, seed particles, methods and coating agents based on the teachings herein.

EXAMPLES

Example 1

Laboratory Fluid Bed Spray Coating of Alkaline Protease/Sodium Citrate Matrix 607 grams of anhydrous sodium sulfate crystals sieved to between 50 and 70 mesh were charged into a Vector FL1 fluid bed coater and fluidized. 2812 grams of an aqueous solution containing 1406 grams of sodium citrate dihydrate was added to 1275 grams of an aqueous protease solution with 19.1% total dry solids and 7.44% w/w active protease. The combined solution contained 85.2% salt based on total dry solids and was allowed to mix for thirty minutes, producing a fine suspension of aggregated proteins. The combined suspension was sprayed onto the sodium sulfate seed particles under the following conditions:

| | |
|---|---|
| Fluid feed rate | 31 g/min |
| Atomization pressure | 54 psi |
| Inlet air temperature set point | 100° C. |
| Outlet air temperature range | 48 to 53° C. |
| Inlet air rate | 74 cfm |

A total of 2078 grams of enzyme granules were harvested as lot A. The overall mass balance for this experiment was 89.1%.

Example 2

Laboratory Fluid Bed Spray Coating of Alkaline Protease/Magnesium Sulfate Matrix 607 grams of anhydrous sodium sulfate crystals sieved to between 50 and 70 mesh were charged into a Vector FL1 fluid bed coater and fluidized. 2812 grams of an aqueous solution containing 1406 grams of magnesium sulfate heptahydrate was added to 1271 grams of an aqueous protease solution with 19.1% total dry solids and 7.44% w/w active protease. The combined solution contained 85.3% salt based on total dry solids and was allowed to mix for thirty minutes, producing a fine suspension of aggregated proteins. The combined suspension was sprayed onto the sodium sulfate seed particles under the following conditions:

| | |
|---|---|
| Fluid feed rate | 29 g/min |
| Atomization pressure | 54 psi |
| Inlet air temperature set point | 100° C. |
| Outlet air temperature range | 47 to 51° C. |
| Inlet air rate | 75 cfm |

A total of 2078 grams of enzyme granules were harvested as lot B. The overall mass balance for this experiment was 81.7%.

Example 3

Laboratory Fluid Bed Spray Coating of Alkaline Protease/Magnesium Sulfate Matrix 542 grams of sucrose crystals sieved to between 35 and 50 mesh were charged into a Vector FL1 fluid bed coater and fluidized. 1709 grams of an aqueous solution containing 588 grams of magnesium sulfate heptahydrate and 147 grams of an ethylated starch marketed under the trade name Ethylex 2015 (A. E. Staley, Decatur, Ill.) that had been fully hydrated by "cooking out" at 190° F. for 15 minutes was added to 952 grams of an aqueous protease solution with 19.7% total dry solids and 8.4% w/w active protease. The combined solution contained 63.7% salt based on total dr solids and was allowed to mix for thirty minutes, producing a fine suspension of aggregated proteins. The combined suspension was sprayed onto the sucrose seed particles under the following conditions:

| | |
|---|---|
| Fluid feed rate | 29 g/min |
| Atomization pressure | 44 psi |
| Inlet air temperature set point | 92° C. |
| Outlet air temperature range | 39 to 44° C. |
| Inlet air rate | 67 cfm |

The coated particles were then coated with 563 grams of an aqueous solution containing 225 grams (40% w/w) of magnesium sulfate heptahydrate. This coating was applied under the following conditions:

| | |
|---|---|
| Fluid feed rate | 30 g/min |
| Atomization pressure | 36 psi |
| Inlet air temperature set point | 84° C. |
| Outlet air temperature range | 39 to 42° C. |
| Inlet air rate | 71 cfm |

The magnesium sulfate coated particles were then cosmetically coated with 2116 grams of an aqueous solution containing 131 grams (6.2% w/w) titanium dioxide, 53 grams (2.5% w/w) methylcellulose marketed under the trade name Methocel A-15LV (Dow Chemical Corp.), 53 grams (2.5% w/w) of maltodextrin M150 (DE=15 from Grain Processing Corp., Muscatine, Iowa), 21 grams (1% w/w) of a non-ionic surfactant marketed as Neodol 23/6.5 (Shell Chemical) and 35 grams (1.67% w/w) of polyethylene glycol at a molecular weight (MW) of 600. The cosmetic coating was applied under the following conditions:

| | |
|---|---|
| Fluid feed rate | 26 g/min |
| Atomization pressure | 56 psi |
| Inlet air temperature set point | 100° C. |
| Outlet air temperature range | 46 to 54° C. |
| Inlet air rate | 75 cfm |

A total of 1710 grams of enzyme granules were harvested as lot C. The overall mass balance for this experiment was 81%.

Example 4

Laboratory Fluid Bed Spray Coating of Alkaline Protease/Magnesium Sulfate Matrix 607 grams of anhydrous sodium sulfate crystals sieved to between 50 and 70 mesh were charged into a Vector FL1 fluid bed coater and fluidized. 2812 grams of an aqueous solution containing 1406 grams of zinc sulfate dihydrate was added to 1272 grams of an aqueous enzyme solution with 19.1% total dry solids and 7.44% w/w active protease. The combined solution contained 85.3% salt based on total dry solids and was allowed to mix for thirty minutes, allowing for complete aggregation of the proteins in solution. The combined solution was sprayed onto the sodium sulfate under the following conditions:

| | |
|---|---|
| Fluid feed rate | 29 g/min |
| Atomization pressure | 54 psi |
| Inlet air temperature set point | 100° C. |
| Outlet air temperature range | 47 to 52° C. |
| Inlet air rate | 75 cfm |

A total of 1840 grams of enzyme granules were harvested as lot D. The overall mass balance for this experiment was 74.8%.

Example 5

Stability of Granules in a Detergent Matrix

The stability of many enzyme granules formulated into bleach-containing detergents is generally excellent, showing generally no more than about 10 to 20% loss in activity over 6 weeks storage at 30 to 37° C. and 70% to 80% R.H. However, to aid in the development and screening of granular formulations, it is desirable to have an accelerated means of determining relative granule stability. The conditions of the accelerated stability test (AST) are far more severe than enzyme granules or detergents would ever encounter in realistic storage or transport. The AST is a "stress test" designed to discriminate differences between formulations which would otherwise not be evident for weeks or months.

In this test, a test detergent base was made from the following ingredients:

| | |
|---|---|
| 72% WFK-1 detergent base | (WFK, Forschunginstitut fuer Reinigungstechnologie e.V., Krefeld, Germany) |
| 25% sodium perborate monohydrate | (Degussa Corp., Allendale Park, New Jersey) |

-continued

| 3% | TAED bleach activator (=tetraacetylethylenediamine) | (Warwick International, Mostyn, UK) |

For each enzyme sample to be tested, three identical tubes were prepared by adding 1 gram of the test base and 30 mg of enzyme granules to a 15 ml conical tube and mixed by inverting the capped tube 5–8 times by hand. A hole was drilled in the tube cap with a ¹⁄₁₆ inch drill bit. One of the three tubes was assayed immediately and the other two were stored in a humidity chamber set at 50° C. and 70% R.H. One of the two stored tubes was assayed after 1 day of storage; the second, after 3 days of storage. Storage stability was reported for Day 1 and Day 3 by dividing the remaining activity by the original activity at Day 0, expressed as a percentage.

The enzyme activity was determined by adding to each tube 30 ml of 0.25M MES pH 5.5 buffer containing 20 μl Catalase HP L5000 (Genencor International, Rochester, N.Y.) and incubating for 40 minutes to inactivate the perborate. After this, the enzyme was assayed by adding 10 μl of the test tube mixture and 10 μl of sAAPF protease substrate to 980 μl of 0.1M Tris pH 8.6, then incubating at 25° C. over 3 minutes, and measuring the optical absorbance at 410 nm. The slope of the absorbance vs. time was then multiplied by the dilution factor and the known extinction coefficient for the specific protease to obtain an enzyme activity as concentration in mg/ml.

Samples of lots made according to Examples 1, 2 and 4 above were subjected to the above accelerated stability test. The data is laid out in Table 1.

TABLE 1

| Sample | Description | Retained activity after 1 day | Retained activity after 3 days |
| --- | --- | --- | --- |
| Example 1 | Sodium citrate matrix | 99.7% | 81.3% |
| Example 2 | Magnesium sulfate matrix | 87.6% | 79.0% |
| Example 4 | Zinc sulfate matrix | 65.6% | 49.6% |

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

What is claimed:

1. A granule, comprising:
   an inert particle and a surrounding layer of an admixture of a protein and a salt, wherein said salt accounts for about between 63.7 and 84.3% of the total weight of said admixture.

2. The granule of claim 1, wherein the salt is selected from the group consisting of an inorganic salt and an organic salt.

3. The granule of claim 1, wherein the protein and salt surrounding layer further includes a binder.

4. The granule of claim 3, wherein the binder is selected from the group consisting of starch, modified starch, carrageenan, gum arabic, guar gum, polyethylene oxide, polyvinyl pyrrolidone, and polyethylene glycol.

5. The granule of claim 1 wherein the protein and salt surrounding layer further comprises a barrier material.

6. The granule of claim 1 further comprising a coating layer located over said surrounding layer.

7. The granule of claim 1 further comprising a coating layer located between the surrounding layer and the inert particle.

8. The granule of claim 6, wherein the coating is selected from the group consisting of polyvinyl alcohol, polyvinyl pyrrolidone, cellulose derivatives such as methylcellulose, hydroxypropyl methylcellulose, hydroxycellulose, ethylcellulose, carboxymethyl cellulose, hydroxypropyl cellulose, polyethylene glycol, polyethylene oxide, chitosan, gum arabic, xanthan and carrageenan.

9. The granule of claim 1, wherein the admixture consists essentially of the protein and the salt.

10. The granule of claim 1, wherein the protein is an enzyme.

11. The granule of claim 1 further comprising a barrier material located over the protein and salt surrounding layer.

12. The granule of claim 10, wherein the enzyme is selected from the group consisting of proteases, amylases, lipases, cellulases and mixtures thereof.

13. The granule of claim 12, wherein the enzyme is a protease.

14. The granule of claim 12, wherein the protease is a subtilisin.

15. The granule of claim 12, wherein the enzyme is a cellulase.

16. The granule of claim 10, wherein the enzyme is selected from the group consisting of oxidases, transferases, dehydratases, reductases, hemicellulases and isomerases.

17. A method of making a granule comprising:
   a. fluidizing inert particles in a fluid-bed coater;
   b. providing a solution or a slurry containing an admixture of protein and salt wherein said salt accounts for about between 63.7 and 85.3% of the total weight of said admixture; and
   c. spraying the solution or slurry on the inert particles to form on the particles a surrounding layer of the admixture of protein and salt.

18. The method of claim 17, wherein the salt is selected from the group consisting of an inorganic salt and an organic salt.

19. The method of claim 17 wherein a binder is mixed in with the admixture of protein and salt.

20. The method of claim 19, wherein the binder is selected from the group consisting of starch, modified starch, carrageenan, gum arabic, guar gum, polyethylene oxide, polyvinyl pyrrolidone, and polyethylene glycol.

21. The method of claim 17 wherein a barrier material is mixed in with the admixture of protein and salt.

22. The method of claim 17 further comprising applying a coating layer over the protein and salt surrounding layer.

23. The method of claim 17 further comprising applying a coating layer between the inert particle and the protein and salt surrounding layer.

24. The method of claim 22, wherein the coating is selected from the group consisting of polyvinyl alcohol, polyvinyl pyrollidone, cellulose derivatives such as methylcellulose, hydroxypropyl methylcellulose, hydroxycellulose, ethylcellulose, polyethylene glycol, polyethylene oxide, chitosan, gum arabic, xanthan and carrageenan.

25. The method of claim 17 further comprising adding a barrier material to form a barrier layer over the protein and salt surrounding layer.

26. The method of claim 17, wherein the protein is an enzyme selected from the group consisting of proteases, amylases, lipases, and cellulases.

* * * * *

UNITED STATES PATENT AND TRADEMARK OFFICE
CERTIFICATE OF CORRECTION

PATENT NO. : 6,423,517 B2
DATED : July 23, 2002
INVENTOR(S) : Becker et al.

It is certified that error appears in the above-identified patent and that said Letters Patent is hereby corrected as shown below:

<u>Title page,</u>
Item [73], Assignee, insert -- Genencor -- in place of "Genecor".

Signed and Sealed this

Fourteenth Day of October, 2003

JAMES E. ROGAN
*Director of the United States Patent and Trademark Office*